US00PP19355P2

(12) United States Plant Patent
Dümmen

(10) Patent No.: US PP19,355 P2
(45) Date of Patent: Oct. 21, 2008

(54) **NEW GUINEA *IMPATIENS* PLANT NAMED 'DUESWEETERS'**

(50) Latin Name: *Impatiens hawkeri*
Varietal Denomination: Duesweeters

(75) Inventor: Tobias Dümmen, Rheinberg (DE)

(73) Assignee: Capitol Green Investments Ltd., Grand Cayman (KY)

( * ) Notice: Subject to any disclaimer, the term of this patent is extended or adjusted under 35 U.S.C. 154(b) by 0 days.

(21) Appl. No.: 11/804,343

(22) Filed: May 17, 2007

(51) Int. Cl.
*A01H 5/00* (2006.01)

(52) U.S. Cl. ..... Plt./318.1
(58) Field of Classification Search ..... Plt./318.1
See application file for complete search history.

*Primary Examiner*—Anne Marie Grunberg
*Assistant Examiner*—Louanne C Krawczewicz My
(74) *Attorney, Agent, or Firm*—C. A. Whealy

(57) ABSTRACT

A new and distinct cultivar of *Impatiens* plant named 'Duesweeters', characterized by its compact, upright and outwardly spreading growth habit; mounded plant habit; freely branching habit; vigorous growth habit; dark green-colored leaves; freely flowering habit; large red and pale pink bi-colored flowers; and good garden performance.

1 Drawing Sheet

Botanical designation: *Impatiens hawkeri.*
Cultivar denomination: 'Duesweeters'.

BACKGROUND OF THE INVENTION

The present invention relates to a new and distinct cultivar of New Guinea *Impatiens,* botanically known as *Impatiens hawkeri* and hereinafter referred to by the name 'Duesweeters'.

The new *Impatiens* is a product of a planned breeding program conducted by the Inventor in Rheinberg, Germany. The objective of the breeding program is to create new compact New Guinea *Impatiens* cultivars with large and attractive flowers.

The new *Impatiens* originated from a cross-pollination made by the Inventor in August, 2003 in Rheinberg, Germany of a proprietary selection of *Impatiens hawkeri* identified as code number 00-0175-13, not patented, as the female, or seed, parent with a proprietary selection of *Impatiens hawkeri* identified as code number E-18-1819, not patented, as the male, or pollen, parent. The new *Impatiens* was discovered and selected by the Inventor as a single flowering plant within the progeny of the stated cross-pollination in a controlled environment in Rheinberg, Germany in May, 2005.

Asexual reproduction of the new *Impatiens* by terminal cuttings in a controlled environment in Rheinberg, Germany since July, 2005, has shown that the unique features of this new *Impatiens* are stable and reproduced true to type in successive generations.

SUMMARY OF THE INVENTION

The cultivar Duesweeters has not been observed under all possible environmental conditions. The phenotype may vary somewhat with variations in environment and cultural practices such as temperature and light intensity without, however, any variance in genotype.

The following traits have been repeatedly observed and are determined to be the unique characteristics of 'Duesweeters'. These characteristics in combination distinguish 'Duesweeters' as a new and distinct cultivar of *Impatiens:*

1. Compact, upright and outwardly spreading growth habit; mounded plant habit.
2. Freely branching habit.
3. Vigorous growth habit.
4. Dark green-colored leaves.
5. Freely flowering habit.
6. Large red and light pink bi-colored flowers.
7. Good garden performance.

Plants of the new *Impatiens* can be compared to plants of the female parent selection. Plants of the new *Impatiens* differ from plants of the female parent selection in the following characteristics:

1. Plants of the new *Impatiens* are more compact than plants of the female parent selection.
2. Plants of the new *Impatiens* and the female parent selection differ in flower color.

Plants of the new *Impatiens* can be compared to plants of the male parent selection. Plants of the new *Impatiens* differ from plants of the male parent selection in the following characteristics:

1. Plants of the new *Impatiens* are more compact than plants of the male parent selection.
2. Plants of the new *Impatiens* have larger flowers than plants of the male parent selection.

Plants of the new *Impatiens* can be compared to plants of the *Impatiens* cultivar Neptis, disclosed in U.S. Plant Pat. No. 10,321. In side-by-side comparisons conducted in Rheinberg, Germany, plants of the new *Impatiens* differed from plants of the cultivar Neptis in the following characteristics:

1. Plants of the new *Impatiens* were more compact than plants of the cultivar Neptis.
2. Plants of the new *Impatiens* had shorter internodes than plants of the cultivar Neptis.
3. Plants of the new *Impatiens* had smaller leaves and shorter petioles than plants of the cultivar Neptis.
4. Plants of the new *Impatiens* had smaller flowers and shorter peduncles than plants of the cultivar Neptis.

BRIEF DESCRIPTION OF THE PHOTOGRAPH

The accompanying colored photograph illustrates the overall appearance of the new *Impatiens,* showing the colors as true as it is reasonably possible to obtain in colored reproductions of this type. Colors in the photograph may differ slightly from the color values cited in the detailed botanical description which accurately describe the colors of the new *Impatiens*. The photograph comprises a side perspective view of a typical flowering plant of 'Duesweeters' grown in a container.

DETAILED BOTANICAL DESCRIPTION

The aforementioned photograph and following observations, measurements and values describe plants grown in Rheinberg, Germany, in containers and under commercial practice during the spring in a glass-covered greenhouse with day and night temperatures averaging 18° C. and light levels averaging 4,500 lux. Plants had been growing for about 16 weeks when the photograph and description were taken. In the following description, color references are made to The Royal Horticultural Society Colour Chart, 2001 Edition, except where general terms of ordinary dictionary significance are used.

Botanical classification: *Impatiens hawkeri* cultivar Duesweeters.

Parentage:

*Female, or seed, parent.*—Proprietary selection of *Impatiens hawkeri* identified as code number 00-0175-13, not patented.

*Male, or pollen, parent.*—Proprietary selection of *Impatiens hawkeri* identified as code number E-18-1819, not patented.

Propagation:

*Type.*—By terminal cuttings.

*Time to initiate roots, summer.*—About seven days at temperatures of 22° C.

*Time to initiate roots, winter.*—About ten days at temperatures of 22° C.

*Time to produce a rooted young plant, summer.*—About 18 days at temperatures of 22° C.

*Time to produce a rooted young plant, winter.*—About 25 days at temperatures of 22° C.

*Root description.*—Fine, fibrous; white in color.

*Rooting habit.*—Freely branching; dense.

Plant description:

*Plant and growth habit.*—Compact, upright to outwardly spreading growth habit; mounded plant habit. Freely branching habit with about nine lateral branches; pinching is typically not required. Moderately vigorous growth habit.

*Plant height.*—About 16 cm.

*Plant diameter.*—About 12 cm.

Lateral branch description:

*Length.*—About 14 cm.

*Diameter.*—About 5 mm.

*Internode length.*—About 3.1 cm.

*Strength.*—Strong.

*Aspect.*—Initially upright to outwardly spreading.

*Texture.*—Smooth, glabrous.

*Color.*—59A.

Foliage description:

*Arrangement.*—Opposite or in whorls; simple.

*Length.*—About 8.3 cm.

*Width.*—About 3.2 cm.

*Shape.*—Ovate.

*Apex.*—Apiculate.

*Base.*—Obtuse.

*Margin.*—Serrulate with ciliation.

*Texture, upper and lower surfaces.*—Smooth, glabrous; leathery.

*Venation pattern.*—Pinnate; arcuate.

*Color.*—Developing and fully expanded foliage, upper surface: 139A; venation, 59A. Developing and fully expanded foliage, lower surface: 59A; venation, 59A.

*Petiole length.*—About 1.3 cm.

*Petiole diameter.*—About 3 mm.

*Petiole texture, upper and lower surfaces.*—Smooth, glabrous.

*Petiole color, upper and lower surfaces.*—59A.

Flower description:

*Flower type and flowering habit.*—Single rounded axillary flowers. Freely flowering habit; usually about six to eight open flowers and flower buds per lateral branch. Flowers positioned above the foliage and typically face upright or outward. Flowers last about one week under greenhouse conditions. Petals self-cleaning, gynoecium persistent. Flowers not fragrant.

*Natural flowering season.*—Year-round under greenhouse conditions. In the garden, flowering from spring until fall in Germany. Plants begin flowering about eight weeks after planting.

*Flower size.*—Length: About 5.6 cm. Diameter: About 5.6 cm. Depth: About 2.3 cm.

*Flower buds.*—Length: About 1.2 cm. Diameter: About 7 mm. Shape: Ovate. Color: 59A tinted with 44B.

*Petals.*—Quantity/arrangement: Five per flower in a single whorl. Length: About 3.1 cm. Width: About 3.2 cm. Shape: Obcordate. Apex: Emarginate; rounded. Base: Acute. Margin: Entire. Texture, upper and lower surfaces: Smooth, glabrous; satiny. Color: When opening and fully opened, upper surface: 55D; central stripes, banner blotch and towards the margins, 44B. When opening and fully opened, lower surface: 40A to 40B.

*Sepals.*—Quantity/arrangement: Three; one modified into an elongated spur. Length: About 1 cm. Width: About 5 mm. Shape: Oval. Apex: Acute. Base: Obtuse. Margin: Entire. Texture, upper and lower surfaces: Smooth, glabrous. Color, upper and lower surfaces: Close to 147A. Spur length: About 4.7 cm. Spur diameter: At flower, about 3 mm; at apex, less than 1 mm. Spur texture: Smooth, glabrous. Spur color: 47B.

*Peduncles.*—Length: About 2.9 cm. Diameter: About 2 mm. Angle: Upright to outward. Strength: Strong; flexible. Texture: Smooth, glabrous. Color: 53A.

*Reproductive organs.*—Stamens: Quantity: Five fused at anthers; filaments free. Anther length: About 5 mm. Anther shape: Oval. Anther color: 155B tinted with 60C. Pollen amount: Abundant. Pollen color: 11D. Pistils: Quantity per flower: One. Pistil length: About 6.5 mm. Stigma shape: Crested. Stigma color: 145D. Style color: 150B. Ovary color: 59A.

*Seed/fruit.*—Seed and fruit production have not been observed.

Disease/pest resistance: Plants of the new *Impatiens* have not been observed to be resistant to pathogens and pests common to New Guinea *Impatiens*.

Garden performance: Plants of the new *Impatiens* have been observed to have good garden performance and tolerate temperatures ranging from about 8° C. to about 35° C.

It is claimed:

1. A new and distinct *Impatiens* plant named 'Duesweeters' as illustrated and described.

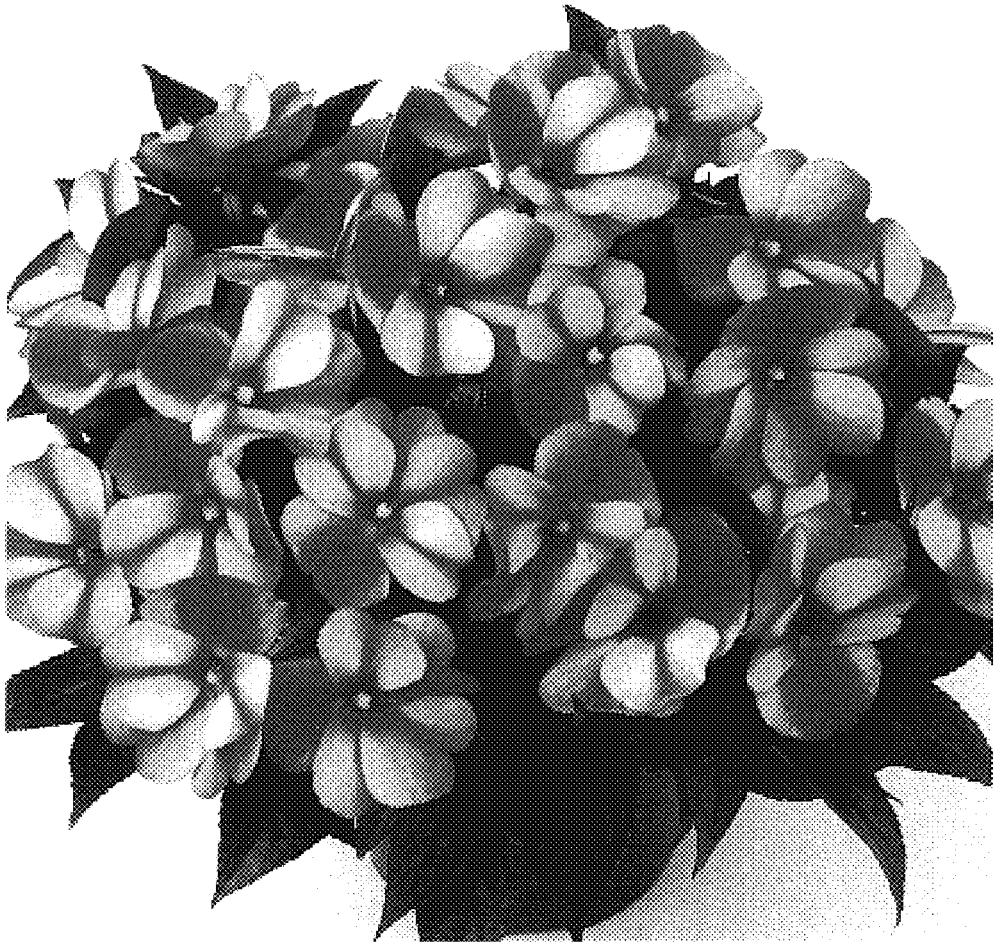

* * * * *